(12) United States Patent
Streeter

(10) Patent No.: US 10,702,044 B2
(45) Date of Patent: Jul. 7, 2020

(54) REVERSIBLE THERMOCHROMIC/PHOTOCHROMIC COSMETIC ACTIVATOR

(71) Applicant: L'OREAL, Paris (FR)

(72) Inventor: John Streeter, Redmond, WA (US)

(73) Assignee: L'OREAL, Paris (FR)

( * ) Notice: Subject to any disclaimer, the term of this patent is extended or adjusted under 35 U.S.C. 154(b) by 918 days.

(21) Appl. No.: 15/198,298

(22) Filed: Jun. 30, 2016

(65) Prior Publication Data
US 2018/0000230 A1 Jan. 4, 2018

(51) Int. Cl.
| | |
|---|---|
| *G06K 15/12* | (2006.01) |
| *A45D 44/00* | (2006.01) |
| *A45D 19/00* | (2006.01) |
| *A45D 34/04* | (2006.01) |
| *A45D 19/16* | (2006.01) |
| *A45D 29/00* | (2006.01) |
| *A45D 40/26* | (2006.01) |
| *A61K 8/02* | (2006.01) |
| *A61K 8/49* | (2006.01) |
| *A61Q 3/02* | (2006.01) |

(Continued)

(52) U.S. Cl.
CPC ............ *A45D 44/00* (2013.01); *A45D 19/00* (2013.01); *A45D 19/16* (2013.01); *A45D 29/00* (2013.01); *A45D 34/04* (2013.01); *A45D 40/26* (2013.01); *A45D 44/005* (2013.01); *A61K 8/0295* (2013.01); *A61K 8/498* (2013.01); *A61Q 3/02* (2013.01); *A61Q 5/065* (2013.01); *A61Q 19/04* (2013.01); *A45D 2029/005* (2013.01); *A45D 2200/15* (2013.01); *A45D 2200/205* (2013.01); *A45D 2200/207* (2013.01); *A61K 2800/438* (2013.01); *A61K 2800/81* (2013.01)

(58) Field of Classification Search
CPC .................... A45D 2200/205; A45D 2029/005
See application file for complete search history.

(56) References Cited

U.S. PATENT DOCUMENTS

| | | | | |
|---|---|---|---|---|
| 6,312,872 B1 * | 11/2001 | Murphy | ................... | B41C 1/05 430/22 |
| 2004/0200496 A1 * | 10/2004 | Choi | ...................... | A45D 29/00 132/200 |

(Continued)

FOREIGN PATENT DOCUMENTS

| | | |
|---|---|---|
| JP | 2006-230436 A | 9/2006 |
| JP | 2008-168062 A | 7/2008 |

OTHER PUBLICATIONS

European Communication pursuant to Rules 161(1) and 162 EPC dated Feb. 6, 2019 in European Patent Application No. 17737441.0, 3 pages.

(Continued)

*Primary Examiner* — Ted W Barnes
(74) *Attorney, Agent, or Firm* — Oblon, McClelland, Maier & Neustadt, L.L.P.

(57) ABSTRACT

A cosmetic activator system for activating a cosmetic is provided including: an activator having an energy source configured to emit an energy pulse and a controller; and an imprinter having an imprint pattern and at least one activation element configured to be in communication with the energy source, wherein the imprinter is configured to create an imprint on the cosmetic.

5 Claims, 4 Drawing Sheets

(51) Int. Cl.
*A61Q 5/06* (2006.01)
*A61Q 19/04* (2006.01)

(56) References Cited

U.S. PATENT DOCUMENTS

| | | | | |
|---|---|---|---|---|
| 2004/0265492 | A1* | 12/2004 | Free | B41M 5/0047 427/256 |
| 2006/0021533 | A1* | 2/2006 | Jeans | B41K 1/02 101/327 |
| 2007/0038270 | A1* | 2/2007 | Ferren | A61N 5/062 607/88 |
| 2008/0058783 | A1* | 3/2008 | Altshuler | A61B 18/20 606/9 |
| 2010/0189960 | A1* | 7/2010 | Yoshida | B41N 1/12 428/156 |
| 2011/0064925 | A1* | 3/2011 | Van Bommel | B82Y 10/00 428/195.1 |
| 2011/0265809 | A1* | 11/2011 | Jeon | A45D 29/00 132/200 |
| 2011/0277338 | A1* | 11/2011 | Li | F26B 3/28 34/275 |
| 2012/0029417 | A1* | 2/2012 | Samain | A61K 8/49 604/20 |
| 2012/0236278 | A1* | 9/2012 | Kwon | G03F 7/2057 355/53 |
| 2012/0244316 | A1* | 9/2012 | Dobler | A61M 35/00 428/141 |
| 2014/0315129 | A1* | 10/2014 | Kidnie | G03F 7/2016 430/273.1 |
| 2015/0182001 | A1* | 7/2015 | Yi | A45D 29/00 132/200 |
| 2015/0283399 | A1* | 10/2015 | Guglielmi | F21V 5/007 604/20 |
| 2015/0335131 | A1* | 11/2015 | Ortiz | A45D 29/00 132/73.6 |
| 2016/0011662 | A1* | 1/2016 | Tanaka | G06F 3/14 345/156 |
| 2016/0174680 | A1 | 6/2016 | Yamasaki | |
| 2016/0227900 | A1* | 8/2016 | Kumagai | A45D 31/00 |
| 2016/0309877 | A1* | 10/2016 | Papshev | A45D 29/00 |
| 2017/0072702 | A1* | 3/2017 | Collett | B41J 3/407 |
| 2017/0215550 | A1* | 8/2017 | Walia | A45D 29/00 |
| 2017/0232669 | A1* | 8/2017 | Watanabe | B29C 67/00 264/496 |
| 2017/0322494 | A1* | 11/2017 | Baldwin | G03F 7/2008 |
| 2018/0049531 | A1* | 2/2018 | Leseman | A45D 19/0008 |
| 2018/0184780 | A1* | 7/2018 | Chevalier | A44C 15/0005 |
| 2018/0196342 | A1* | 7/2018 | Miller | G03F 1/42 |
| 2019/0030946 | A1* | 1/2019 | Zhang | B44C 1/24 |

OTHER PUBLICATIONS

International Search Report and Written Opinion dated Oct. 20, 2017 in PCT/US2017/039617.

* cited by examiner

REVERSIBLE THERMOCHROMIC/PHOTOCHROMIC COSMETIC ACTIVATOR

BACKGROUND

Field

The present application is directed to a system and method for activating a cosmetic coating with fine precision.

SUMMARY

In an embodiment, a cosmetic activator system for activating a cosmetic is provided including: an activator having an energy source configured to emit an energy pulse and a controller; and an imprinter having an imprint pattern and at least one activation element configured to be in communication with the energy source, wherein the imprinter is configured to create an imprint on the cosmetic.

In an embodiment, the imprinter includes an array of activation elements.

In an embodiment, the imprinter includes a raised surface and an array of activation elements, wherein the imprint pattern is based on the raised surface and the array of activation elements.

In an embodiment, the imprinter includes a raised surface and the imprint pattern is based on the raised surface.

In an embodiment, the cosmetic activator system further includes a timer, wherein the controller is configured to control the energy source based on the timer.

In an embodiment, the activation element is at least one of a heating element, a photo element, and an electrical element.

In an embodiment, the controller is configured to control the energy source based on the activation element.

In an embodiment, the imprinter further includes a cosmetic layer, wherein the system can be configured to simultaneously apply and activate the cosmetic layer.

In an embodiment, the activator further includes at least one of a clip and a ring, wherein the cosmetic activator system is configured to be wearable.

In an embodiment, an imprinter for patterning a cosmetic is provided including: an imprint pattern; and at least one activation element configured to be in communication with an energy source, wherein, when the activation element is energized, an imprint is patterned on the cosmetic based on the imprint pattern.

In an embodiment, the activation element is at least one of a heating element, a photo element, and an electrical element.

In an embodiment, the imprinter includes an array of activation elements.

In an embodiment, the imprinter further includes a cosmetic layer, wherein the imprinter can be configured to simultaneously apply and activate the cosmetic layer.

BRIEF DESCRIPTION OF THE DRAWINGS

A more complete appreciation of the embodiments and many of the attendant advantages thereof will be readily obtained as the same becomes better understood by reference to the following detailed description when considered in connection with the accompanying drawings, wherein.

DETAILED DESCRIPTION

Figure 1A:
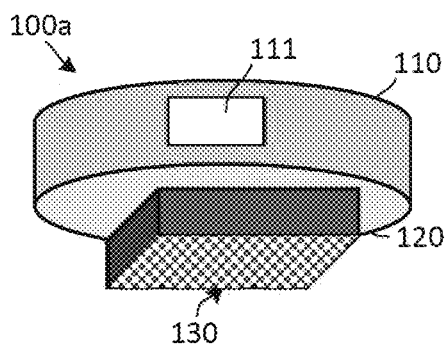
FIG. 1A shows a drawing of an cosmetic activator system including an activator in communication with an imprinter having an imprint pattern according to an example.

The present disclosure relates to an cosmetic activator system configured to activate a cosmetic coating with fine precision. Examples of cosmetics include thermochromic materials, such as Leuco dyes, and thermochromatic liquid crystals (TLC), and photochromic materials such as spiropyrans. In an aspect, activation of the cosmetic can be reversible or irreversible. In an example, the cosmetic can be applied as a coating to a fingernail, a portion of skin, and a grouping of hair.

Activation

Activation of the cosmetic can be one of a modification of a chemical state, an absolute or relative temperature, an oxidation state, a photochromic state, and a crystalline structure. In an aspect, the activation can include a first activation of the cosmetic, as well as a second activation configured to reverse or reset the first activation of the cosmetic in the case of a reversible activation or modification.

Cosmetics including thermochromic materials can be activated by one or more temperatures and durations. In an example, the activation by modification of temperature can be based on a glass-transition temperature and vitrification of a property of the cosmetic. The activation by modification of temperature can include a temperature range and duration. A transition temperature near or above body temperature may assure the activation and prevention of reversal. Reversal temperatures in the extreme cold (0-5° C.) limit chance of premature or unintentional reversal without an artificial application of freeze spray or other. For example, the activation by modification of temperature can include a first temperature range (e.g. 37° C.-40° C.) where the first temperature range is held for a first duration (e.g. 2-5 sec). In an aspect, the first activation can be reset by a second activation with a second temperature range (e.g. 0° C.-5° C.) where the second temperature range is held for a second duration (e.g. 5-10 sec).

In an aspect, one or more temperature ranges can be based on a property of the cosmetic such that the cosmetic is configured to have one or more colors for each respective temperature range. Each temperature range is preferably within a safety threshold to prevent tissue injury. However, for short durations, the temperature range may also exceed the safety threshold.

The activation by the oxidation change can include one of a voltage potential or a charge amount. The activation by the photochromic change can include exposure to specific types of light of sufficient intensity such as ultraviolet (UV) radiation. In an example, the activation of the cosmetic can be a surface topography change, such as a reflectance property.

Referring now to the drawings, wherein like reference numerals designate identical or corresponding parts throughout the several views.

Cosmetic Activator System

FIG. 1A shows a drawing of a cosmetic activator system 100a including an activator 110 in communication with an imprinter 120 having an imprint pattern 130 according to an example. The activator includes an energy source and a controller in communication with the energy source and the imprinter. The activator can further include a user interface 111, a timer, and processing circuitry. In an example, the user interface 111 can have a display and one or more buttons (not shown) for a user input. Examples, of the user input can include one or more control operations for using the cosmetic activator system such as controlling power, starting and ending an activation, and identifying the imprinter, etc.

Figure 1B:
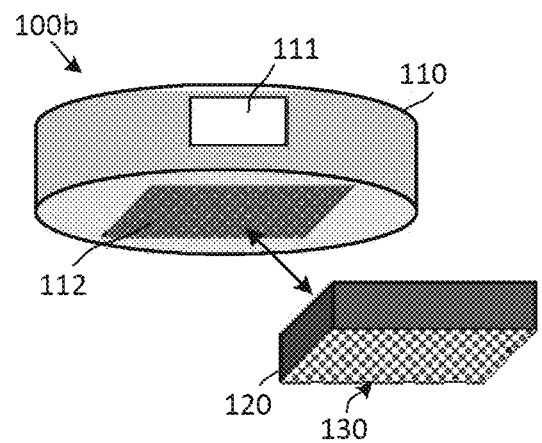
FIG. 1B shows a drawing of the imprinter separated from the activator and exposing an attachment area according to an example.

The cosmetic activator system can be a single piece or a combination of two or more pieces. In an example, the imprinter 120 can be configured to attach to the activator 110 at an attachment area 112 (See FIG. 1B). The attachment area 112 can be configured to communicate or transfer activation energy from the activator 110 to the imprinter 120. The activator can be configured to start and end an activation step by at least one of the controller, the user interface, the timer, and the processing circuitry.

The cosmetic activator system further includes at least one activation element, which can be in either the activator or the imprinter. Examples of an activation element include a thermoelectric element, a photo element, and an electrical element. The cosmetic activator system can also include a linear array of activation elements or a spatial array of activation elements. In an aspect a precision of the image pattern can be based on a number of activating elements in an array of activating elements. In an example the precision of the image pattern can configured to create an image without noticeable pixilation as well as text with different fonts and embellishments. In a preferred embodiment, the activation elements are integrated into the imprinter. In an aspect, a set of imprinters can be interchanged with the activator, where each imprinter can be configured to match with at least one of a respective cosmetic and activation modality. In an example, the controller of the activator can be configured to recognize the activation modality of the imprinter. In an example, the user interface can be configured to receive the activation modality of the imprinter.

Figure 1C:
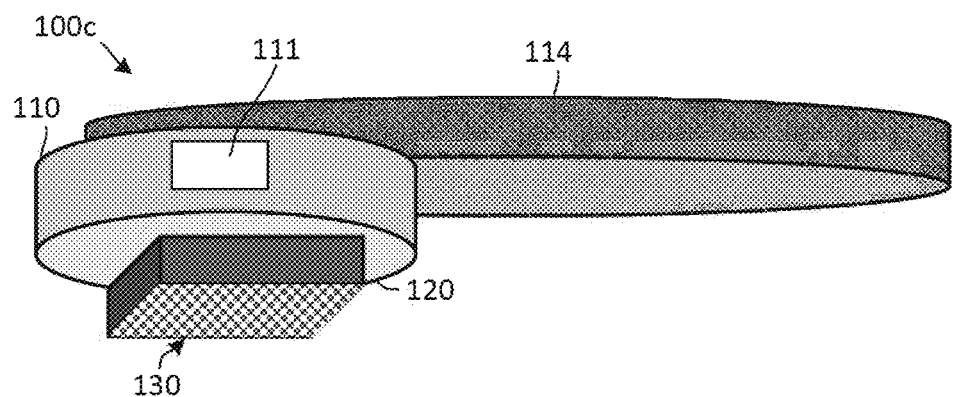
FIG. 1C shows a drawing of the cosmetic activator system including a handle according to an example.
Figure 1D:
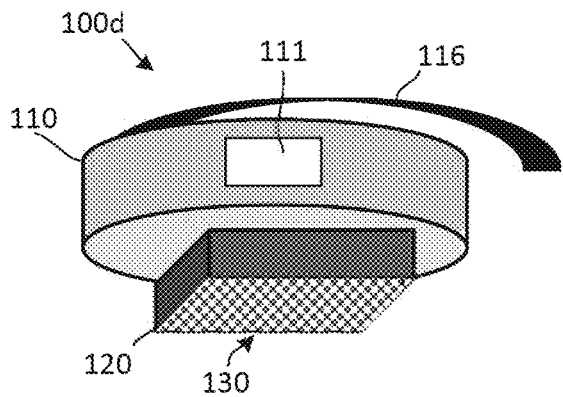
FIG. 1D shows a drawing of the cosmetic activator system including a clip according to an example.
Figure 1E:
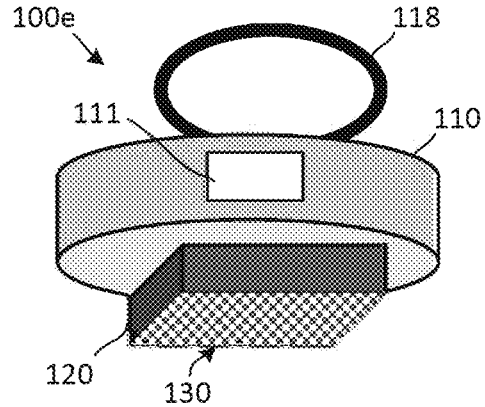
FIG. 1E shows a drawing of the cosmetic activator system including a ring according to an example.

The cosmetic activator system 100 can optionally further include ergonomic and attachment features. For instance, the activator can include a handle 114 for gripping (See FIGS. 1C, 3A), a clip 116 for clasping (See FIG. 1D), and a ring 118 configured for wearing on a finger or wrist (See FIG. 1E).

Figure 3A:
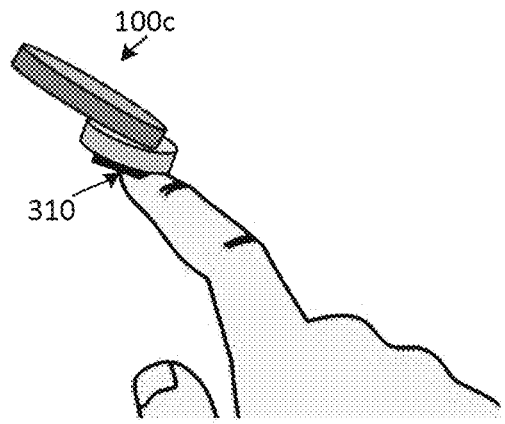
FIG. 3A shows a drawing of the cosmetic activator system configured to apply the imprint pattern on a fingernail of a finger according to an example.

The handle 114 can be configured to aid in applying an imprint pattern 130 on a fingernail 310 of a finger (See FIG. 3A). The clip 116 can be used as an attachment means. In an example, the clip 116 can be configured to allow the cosmetic activator system 100d to be wearable. In an example, the clip 116 can be configured to clasp to a portion of hair 320. In an aspect, the clip 116 can be configured to maintain a grouping of hair such that a spatial position of the imprint is also maintained on the grouping of hair. The clip 116 can have different shapes and be configured to attach to any side of the activator. In an example, the cosmetic activator system can be configured to adhere to a user's skin or nails.

Imprinter

Figure 2A:
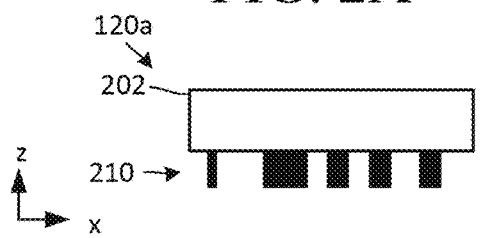
FIG. 2A shows a drawing of an imprinter having a raised surface configured for generating the imprint pattern with fine precision according to an example.
Figure 2B:
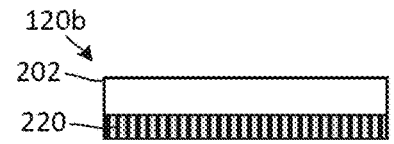
FIG. 2B shows a drawing of an imprinter including an array of activating elements for generating the imprint pattern with fine precision according to an example.
Figure 2C:
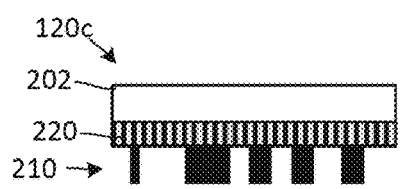
FIG. 2C shows a drawing of an imprinter including the array of activating elements and the raised surface for generating the imprint pattern with fine precision according to an example.
Figure 2D:
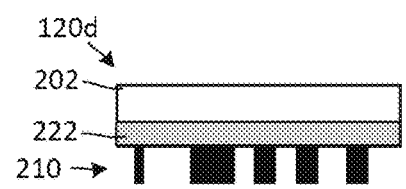
FIG. 2D shows a drawing of an imprinter including a single activating element and the raised surface for generating the imprint pattern with fine precision according to an example.

The imprinter 120 can be of several types including a passive imprinter (See FIG. 2A), an active imprinter (See FIGS. 2B, 2E, 2F, 2G), and a hybrid imprinter (See FIGS. 2C, 2D). Each imprinter 120 has a distal portion 202 that is configured to interface with the attachment area 112 of the activator 110.

The passive imprinter can have a raised surface 210 configured to make the imprint pattern. Examples of the passive imprinter include a stamp, a mold, and a branding iron. The raised surface 210 can be created in a variety of ways. The raised surface 210 can be created manually or in an automated fashion such as a 3D printer and a computer numeric control (CNC) machine.

An active imprinter can include an array of activating elements 220 for generating the imprint pattern with fine precision to a cosmetic 240 (See FIG. 2B).

Figure 2E:
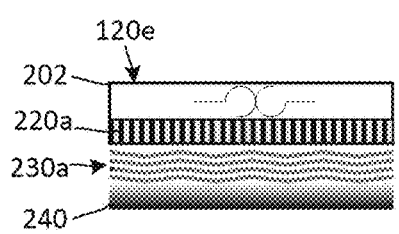
FIG. 2E shows a drawing of an imprinter including an array of heating elements configured to generate the imprint in a cosmetic coating using fine precision heat according to an example.

As shown in FIG. 2E, an active imprinter 120e can include an array of heating elements 220a configured to generate fine precision heating 230a to the cosmetic 240. Alternatively, the heating element can be a fine wire for manually tracing the imprint pattern on the cosmetic.

Figure 2F:
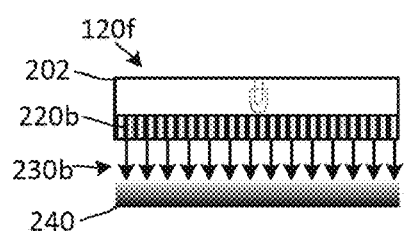
FIG. 2F shows a drawing of an imprinter including an array of photo elements configured to generate the imprint in the cosmetic coating using fine precision light according to an example.

As shown in FIG. 2F, an active imprinter 120f can include an array of photo elements 220b configured to generate fine precision lighting 230b to the cosmetic 240. In an example, a photo element can be a focused light such as a laser configured to trace a programmed imprint. In another example a photo element can be a laser configured to manually create the imprint.

Figure 2G:
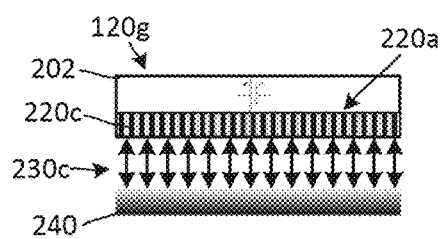
FIG. 2G shows a drawing of an imprinter including an array of electrical elements configured to generate the imprint in the cosmetic coating using fine precision electrical charge according to an example.

As shown in FIG. 2G, an active imprinter 120g can include an array of electrical elements 220c configured to generate fine precision electric charge 230c to the cosmetic 240.

Figure 2H:
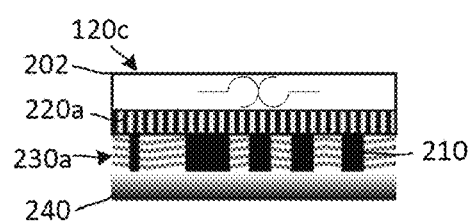
FIG. 2H shows a drawing of an imprinter including an array of heating elements and the raised surface configured to generate an imprint in the cosmetic coating using fine precision heating according to an example.

A hybrid imprinter can be a combination of an active imprinter and a passive imprinter in several ways. In a first example, the array of activating elements 220 of an active imprinter can be configured to activate the cosmetic 240 in conjunction with the raised surface 210 of the passive imprinter (See FIGS. 2C, 2H). In a second example, an active imprinter can have a single activating element 222 configured to activate the cosmetic 240 in conjunction with the raised surface 210 of the passive imprinter (See FIG. 2D). According to an example, the precision of the image pattern can be based on a hybrid imprinter having a combination of the array of activating elements and the raised surface 210 of the passive imprinter.

Figure 3B:
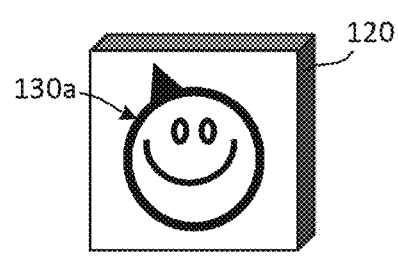
FIG. 3B shows a drawing of an imprinter having a imprint pattern of an image and an outline of a fingernail with an imprint reflecting the imprint pattern according to an example.
Figure 3B:
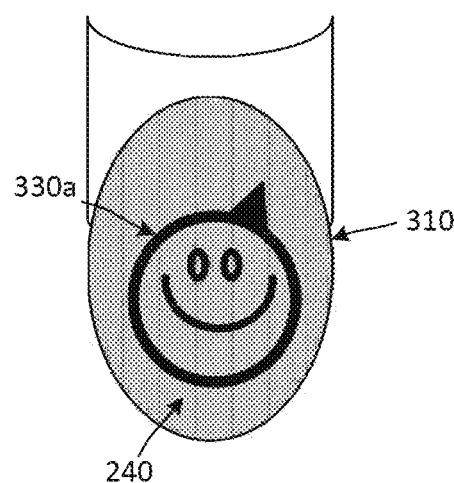
Figure 3C:
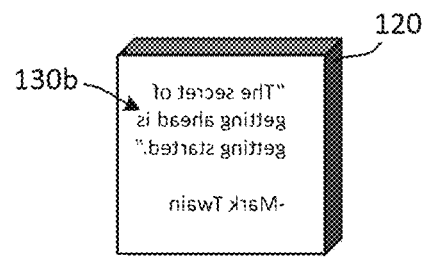
FIG. 3C shows a drawing of an imprinter having a imprint pattern of a series of words and an outline of a fingernail with an imprint reflecting the imprint pattern according to an example.
Figure 3C:
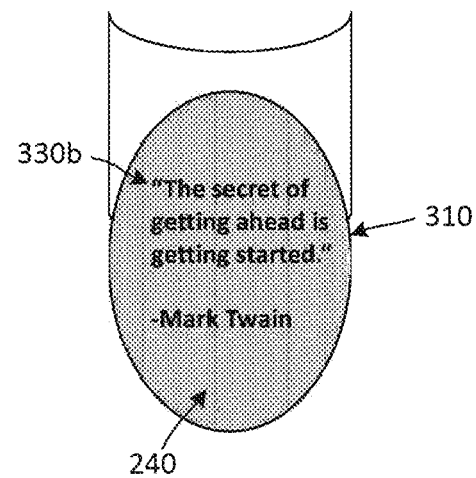

The imprinter can be configured to have a mirror image of the image pattern 130 such that an imprint 330 is reflected on the cosmetic as intended (See FIGS. 3B, 3C).

Figure 2I:
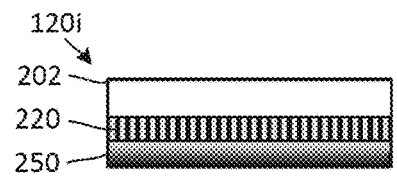
FIG. 2I shows a drawing of the imprinter further including an attached cosmetic layer, where the imprinter is configured to apply a patterned cosmetic based on the image pattern according to an example.

In an embodiment, the imprinter can further include a cosmetic layer 250, where the cosmetic activator system can be configured to simultaneously apply and pattern the cosmetic according to an example (See FIG. 2I). In an aspect, the imprinter including the cosmetic can be a disposable unit.

Imprint Pattern

The imprint pattern can be of an image and text with different fonts and embellishments. The imprint pattern can be configured to transfer to a cosmetic coating on a fingernail, a portion of skin, and a grouping of hair. FIG. 3B shows a drawing of an imprinter 120 having a imprint pattern 130a of an image and an outline of a fingernail 310 with an imprint 330a reflecting the imprint pattern 130a. FIG. 3C shows a drawing of an imprinter 120 having a imprint pattern 130b of a set of words and an outline of a fingernail 310 with an imprint 330b reflecting the imprint pattern 130b. In an aspect, the imprint pattern can patterned on a cosmetic coated on a transfer material, which can subsequently applied to the user.

Activation Process

Figure 4A:
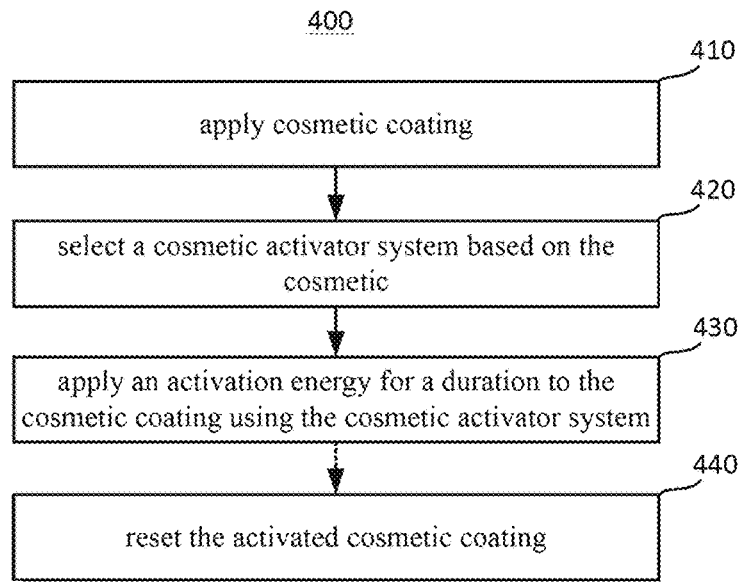
FIG. 4A shows a flow diagram describing a series of steps in a method for activation of a cosmetic according to an example.

FIG. 4A shows a flow diagram describing a series of steps in a method 400 for activation of a cosmetic according to an example.

At step 410, apply a cosmetic coating. The step of applying a cosmetic coating can be done in several ways. In an example, the cosmetic can be brushed on a fingernail or portion of skin similar to nail polish (See FIGS. 3B, 3C). In an example, the cosmetic can be sprayed on a fingernail, portion of skin, or grouping of hair.

At step 420, select a cosmetic activator system based on the cosmetic. The step of selecting a cosmetic activator system based on the cosmetic can be done in several ways. The cosmetic activator system may be packaged along with the cosmetic according to an example. The cosmetic can be marked for compatibility with a cosmetic activator system.

Figure 4B:
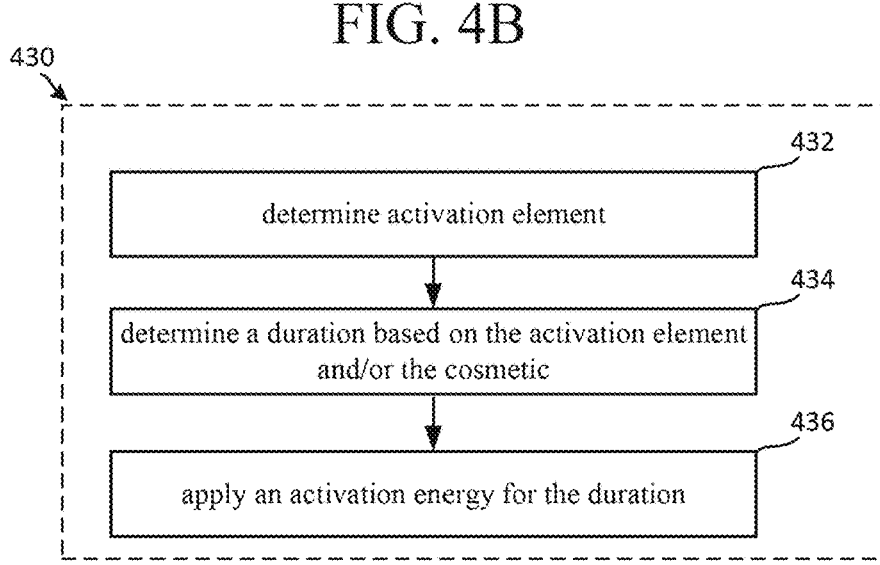
FIG. 4B shows a flow diagram for describing a series of steps for applying an activation energy for a duration to the cosmetic.

At step 430, apply an activation energy for a duration to the cosmetic coating using the cosmetic activator system. The step of applying an activation energy for a duration to the cosmetic coating using the cosmetic activator system can be done based on the cosmetic activation modality. FIG. 4B shows a flow diagram for a set of steps to carry out step 430. At step 432, determine the activation element. In an example, the controller of the activator can be configured to recognize the activation element. At step 434, determine a duration based on the activation element and/or the cosmetic. In an example, the controller of the activator can be configured to recognize the duration based on the activation element and/or the cosmetic. Alternatively, the user can input the duration into the activator. At step, 436, apply an activation energy for the duration. After step 436, a imprint 330 is made on the cosmetic.

Figure 4C:
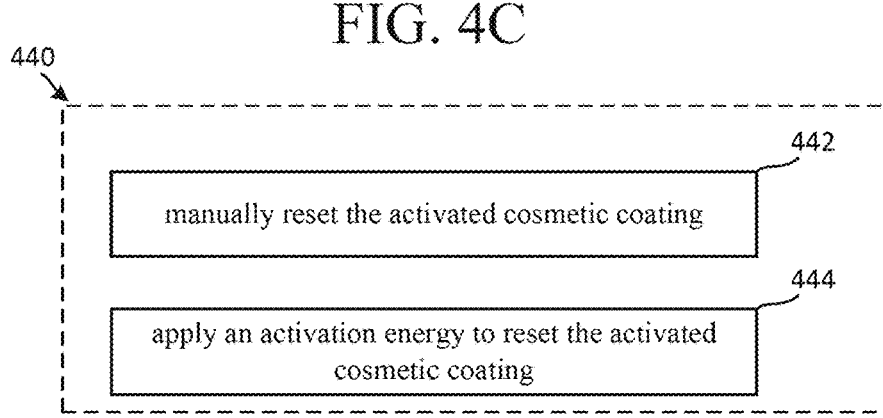
FIG. 4C shows different examples of resetting an activated cosmetic coating.

Optionally, at step 440, the method 400 can include resetting the activated cosmetic coating. The resetting of the activated cosmetic coating can be done in several ways as shown in FIG. 4C. In an example, the activated cosmetic coating can be reset manually (442). In an example, the manual resetting can be done by a thermal change with a cold temperature exposure such as water, ice, or cooled spray. In another example, the activated cosmetic coating can be reset by applying an activation energy using the cosmetic activator system. By resetting the cosmetic, the cosmetic coating can be activated by step 430 again.

Obviously, numerous modifications and variations of the present invention are possible in light of the above teachings. It is therefore to be understood that within the scope of the appended claims, the invention may be practiced otherwise than as specifically described herein.

The invention claimed is:

1. A cosmetic activator system for activating a cosmetic comprising:
   an activator having an energy source configured to emit an energy pulse and a controller; and
   an imprinter having an imprint pattern and at least one activation element configured to be in communication with the energy source, wherein the imprinter is configured to create an imprint on the cosmetic based on direct contact with the cosmetic,
   wherein the activator further includes at least one of a clip and a ring, wherein the cosmetic activator system is configured to be wearable.

2. The system of claim 1, wherein the imprinter includes an array of activation elements.

3. The system, of claim 1, further including a timer, wherein the controller is configured to control the energy source based on the timer.

4. The system of claim 1, wherein the activation element is a photo element.

5. The system of claim 4, wherein the controller is configured to control the energy source based on the activation element.

* * * * *